United States Patent [19]

Aldred et al.

[11] 4,368,980

[45] Jan. 18, 1983

[54] APPARATUS FOR DETECTING AN AQUEOUS LIQUID IN BOTTLES AND CONTAINERS

[76] Inventors: Phillip J. E. Aldred, 34 East St., Saffron Waldon, Essex; Peter J. Taylor, 31 Old Forge Way, Sawston, Cambridgeshire; Bryan W. Kenzie, 6 Emsons Close, Linton, Cambridgeshire, all of England

[21] Appl. No.: 162,257

[22] Filed: Jun. 23, 1980

[30] Foreign Application Priority Data

Jun. 28, 1979 [GB] United Kingdom ............... 7922502

[51] Int. Cl.$^3$ ..................... G01N 21/90; B07C 5/342
[52] U.S. Cl. ................... 356/240; 209/524; 209/582; 250/223 B; 356/407
[58] Field of Search ............... 356/240, 407; 250/339, 250/223 B; 209/524, 582

[56] References Cited

U.S. PATENT DOCUMENTS

| | | | |
|---|---|---|---|
| 3,405,268 | 10/1968 | Brunton | 250/239 |
| 3,497,304 | 2/1970 | Berube | 356/407 |
| 3,821,550 | 6/1974 | Priest | 250/239 |
| 4,121,103 | 10/1978 | Calhoun | 250/343 |
| 4,262,196 | 4/1981 | Smith | 356/240 |
| 4,300,689 | 11/1981 | Franklin et al. | 356/407 |

*Primary Examiner*—Vincent P. McGraw
*Attorney, Agent, or Firm*—Brisebois & Kruger

[57] ABSTRACT

The invention relates to apparatus for detecting water-based residues in translucent bottles, in which energy in two parts of the spectrum in and near the infra-red region, in one of which parts (0.8 to 0.9 microns) water is relatively transparent and the other of which parts (1.2 to 1.6 microns) water is more strongly absorbent is transmitted through a bottle, and the intensities of the emergent energies in the two parts are separately measured by a silicon detector and a germanium detector, associated with respective collimator tubes and filters, and are compared to produce a signal indicative of the presence of water in the bottle.

4 Claims, 5 Drawing Figures

APPARATUS FOR DETECTING AN AQUEOUS LIQUID IN BOTTLES AND CONTAINERS

The present invention relates to apparatus for detecting an aqueous liquid in translucent bottles and containers (hereinafter generally called "bottles"), and particularly to the detection of liquid residues in bottles which have been washed in a caustic solution prior to filling with beer, soft drinks or other products.

BACKGROUND OF THE INVENTION

The specification of U.S. Pat. No. 4121103 describes an inspection system based on the absorption of infra-red radiation by water, which is the main constituent of liquid residues, in which light rays including energy in the infra-red region are directed upwards through the bottom of a bottle to be inspected and on to a detection means for detecting the energy of particular infra-red wavelengths which is absorbed if there is any liquid residue in the bottle, thereby to produce a signal to reject any bottle which contains an aqueous residue.

Such a system can operate satisfactorily when inspecting clear bottles, but it cannot satisfactorily inspect coloured bottles which also absorb radiation in or near the infra-red region. Different bottles of the same colour can vary considerably in their absorption of infrared radiation. The ranges of observed transmission coefficients for different coloured bottles, at the wavelength used for infra-red measurement, are:

for clear bottles—0.5–0.99
for amber bottles—0.09–0.35
for green bottles—0.008–0.61

For these reasons a simple measurement of transmitted intensity will not give a reliable indication of water content. The present invention has for an object to alleviate these difficulties and provide an inspection system for coloured and clear bottles and which is capable of use where differently coloured bottles, as well as clear bottles, are inspected on the same line.

SUMMARY OF THE INVENTION

In the detection system according to the invention the intensities of the energy transmitted through a bottle in two parts of the spectrum in and near the infra-red region, in one of which water is relatively transparent and in the other of which water absorbs more strongly, are compared to provide a signal indicative of an aqueous residue in the bottle.

The inspection apparatus conveniently uses two detectors, preferably of different types, to measure the transmitted intensity in the two parts of the spectrum.

Thus while first detector which is sensitive in a first part of the spectrum, e.g. about 0.8 to about 0.9 microns, in which water is fairly transparent, and which therefore essentially measures the absorption by the glass, and the second detector which is sensitive in a second part of the spectrum, e.g. about 1.2 to about 1.6 microns, in which water is more strongly absorbent and which measures the absorption by both the glass and any water present, the ratio intensity of energy received by second detector/intensity of energy received by first detector is sensitive to water content but insensitive to variations in thickness or colour of the glass.

Although the compensation is not perfect since the compensation measurement is taken at a different wavelength to the water measurement, and the infra-red absorption characteristics of differently coloured glasses have different shapes, experimental results have shown that the degree of compensation is adequate for practical purposes.

In one embodiment, one detector, conveniently a silicon detector with a filter to limit its short wavelength response, measures the intensity at 0.85 microns where water is relatively transparent. This detector therefore measures the absorption by the glass of the bottle and provides a calibration signal. The other detector, conveniently a germanium detector with a silicon filter to limit its short wavelength response, measures the intensity in the range of 1.2 to 1.6 microns where water absorbs more strongly.

A pass/fail decision is based on the ratio of the outputs of the two detectors, i.e.

fail if $I_{Ge} < nI_{Si}$ where $I_{Ge}$ and $I_{Si}$ are respectively the intensities measured by the germanium and silicon detectors and n is a constant, the value of which is determined by the relative intrinsic sensitivities of the detectors. The value of n can be chosen to give the desired sensitivity of the system since an increase in n will decrease the amount of water required for a bottle to fail, and vice versa.

The use of the second wavelength to calibrate the bottles, in effect, reduces the variation which, as indicated by the above observed transmission coefficients, exceeds 100:1 between the most absorbing green bottle and the least absorbing clear bottle, to the range of 2.5:1, and ensures that all bottles, whatever their colour, fail if they contain a minimal depth of water, for example, between 1 mm and 4 mm of water.

DESCRIPTION OF THE PREFERRED EMBODIMENT

Figure 1:
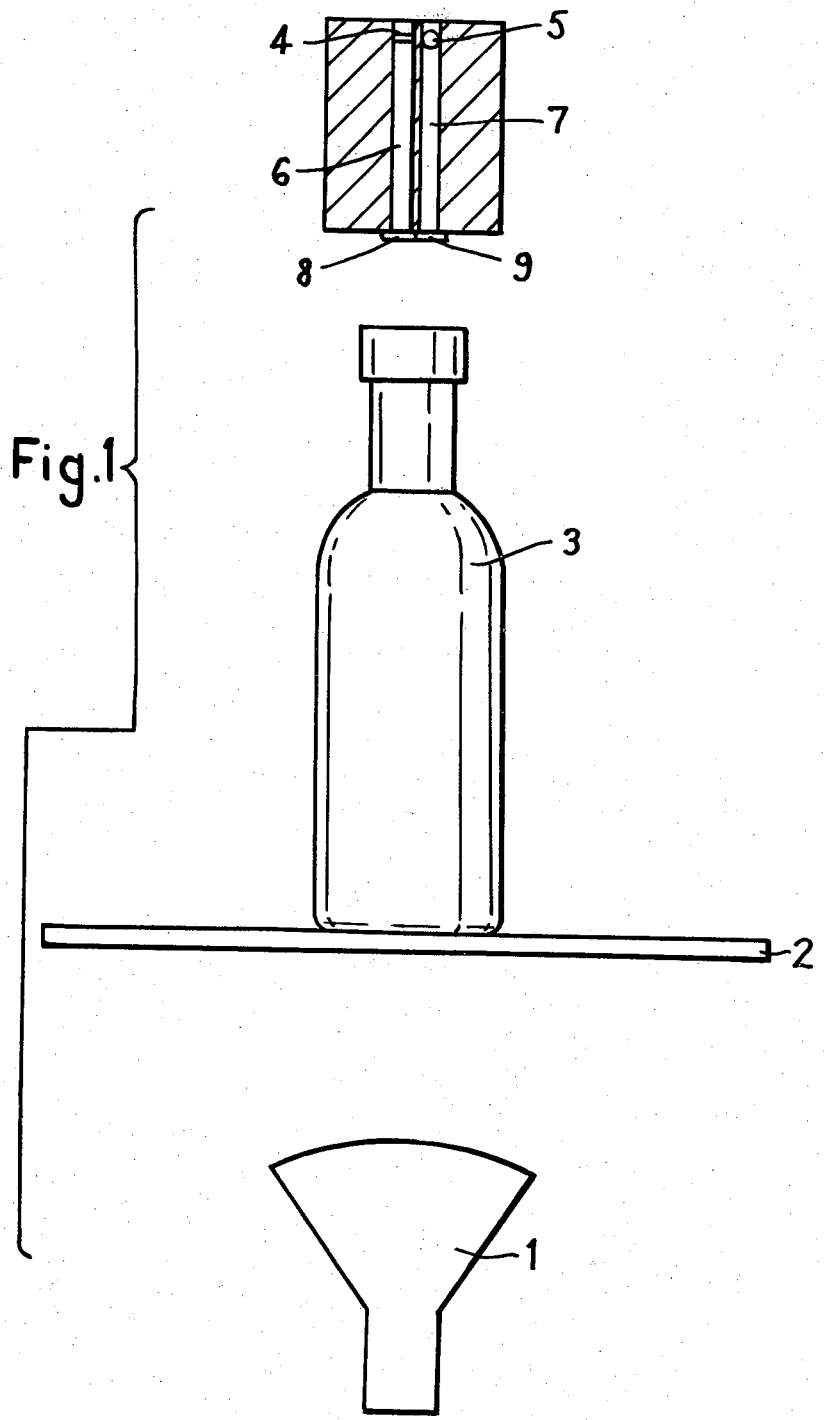
FIG. 1 is a schematic diagram of the detector apparatus.

Referring to FIG. 1 the radiation from a filament lamp 1 located beneath a diffuser 2 passes axially upwards through the bottle 3 to be inspected. Above the bottle the silicon detector 4 and the germanium detector 5 are mounted towards the upper end of simple collimator tubes 6,7, their respective filters 8,9 being mounted at the lower ends of the collimator tubes. This ensures that only radiation which has passed through the base of the bottle is detected. Filter 8 may, for example, be a Kodak Wratten No. 87 filter, and filter 9 is silicon filter and may comprise a 0.75 mm thick slice from a single crystal of silicon. The silicon detector may be a silicon photodiode whilst the germanium detector may be a germanium phototransistor.

Figure 4:
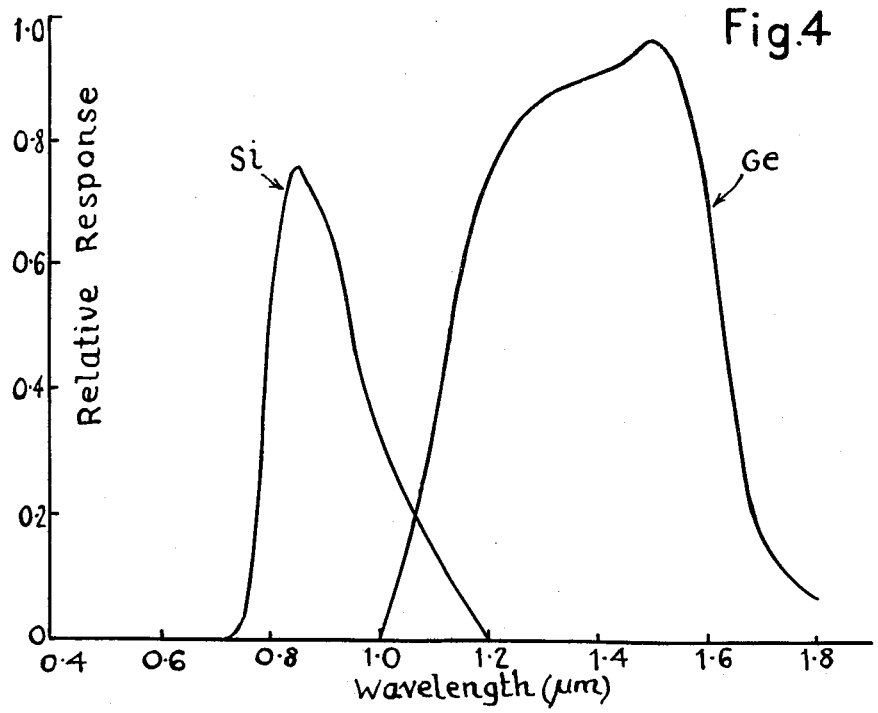
FIG. 4 shows the transmission characteristics of the two detector/filter combinations used in the inspection system.

FIG. 4 shows the spectral response of the two detector/filter combinations used in the detector system. Curve Si is the relative response of the silicon detector with Kodak Wratten No. 87 filter and curve Ge is the relative response of the germanium detector with a silicon filter.

Figure 5:
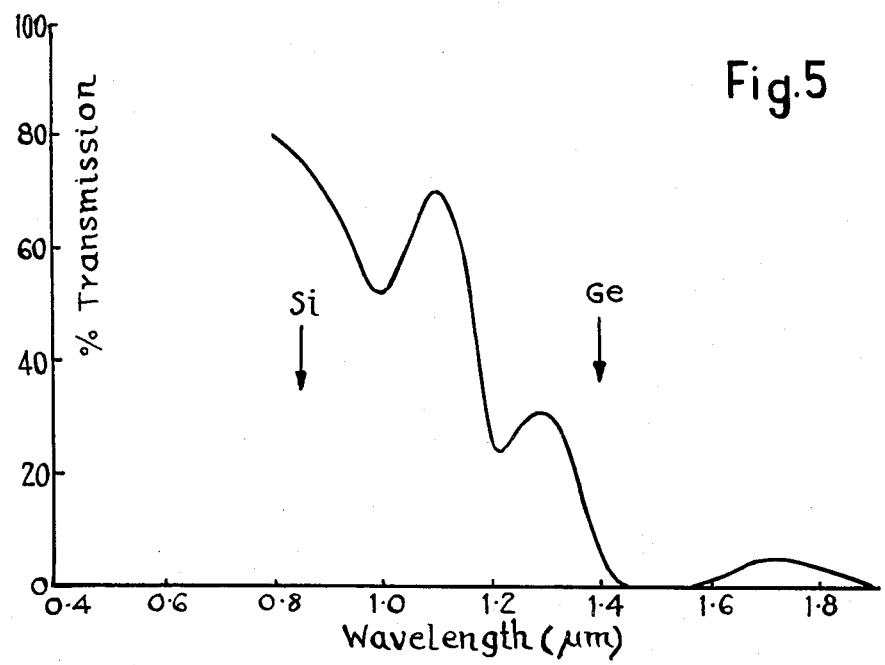
FIG. 5 is a graph showing the transmission of radiation of water as a function of wavelength in the infra-red region of the spectrum.

FIG. 5 shows a graph of the transmission of radiation by water as a function of wavelength. The calibration and measuring wavelengths are indicated by the arrows Si and Ge respectively.

Figure 2:
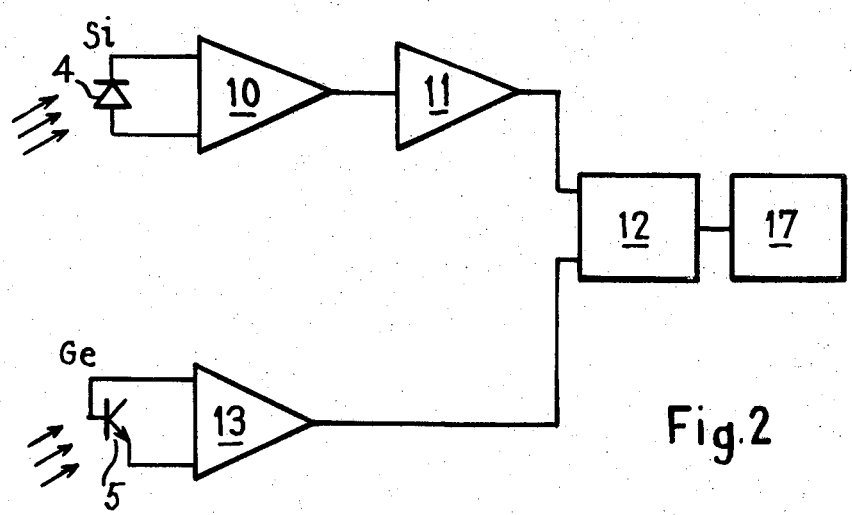
FIG. 2 is a block diagram of one embodiment of electronic circuit for use with the detector apparatus.

Referring to FIG. 2, the output from the silicon detector 4, after amplification in the amplifier 10, is fed to a variable gain amplifier 11, the output from which is compared in a comparator 12 with the output from the germanium detector 5, after amplification in an amplifier 13.

The output from the comparator is fed to a responder 17 which responds when the comparator output departs from a predetermined value.

Figure 3:
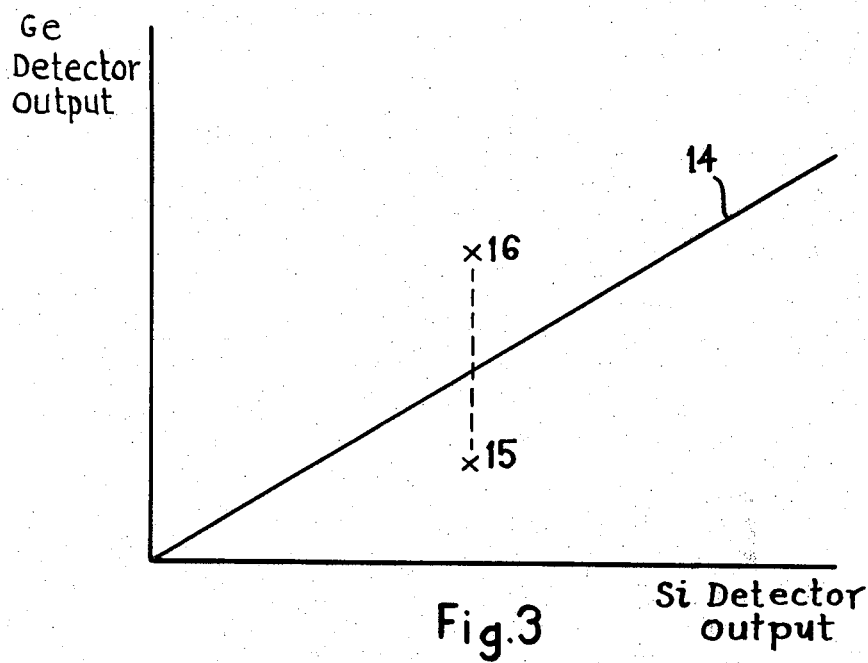
FIG. 3 is a diagram showing the pass/fail criterion.

If the germanium detector response is reduced, due to water-based liquid residue in the bottle, below the pass-fail line 14 in FIG. 3, e.g. to the point 15, the bottle would fail. The response from a typical empty bottle is at point 16 and the bottle would pass. The slope of the line 14 can be adjusted by the sensitivity control amplifier 11. The responder 17 can control a bottle inspection reject mechanism.

The liquid detector may be mounted next to the main station of an inspection apparatus for detecting foreign bodies in bottles, such as described in U.S. Pat. No. 3,727,068, or built into such apparatus, and the output from the responder 17 may be used to control a common reject mechanism.

We claim:

1. Apparatus for inspecting intermixed clear and differently colored translucent bottles prior to filling with a beverage and including means for detecting the presence of an aqueous liquid residue left in both clear and differently colored translucent bottles from a preceding washing operation, said detector means comprising (a) means for directing, through an area of the bottle wall against which any such residue collects energy in two parts of the spectrum in and near the infra-red region, in one of which parts water is relatively transparent and in the other of which parts water is more strongly absorbent, (b) first and second radiant energy detectors and associated collimator tube means arranged to receive radiant energy which has passed through substantially the same part of said area of the bottle wall, (c) filter means associated with said detectors for causing said first and second detectors to produce respective signal outputs of intensities corresponding to the intensities of the energy in said one part and said other part of the spectrum respectively, (d) comparator means for comparing the said signal outputs and producing a comparator signal corresponding to the ratio of the intensities of said output signals and (e) responder means responsive to said comparator signal and operative to produce a bottle reject signal, independent of bottle color, upon the comparator signal ratio:

intensity of output signal from said second detector/intensity of output signal from said first detector falling below a predetermined value.

2. Apparatus according to claim 1, wherein said first and second detectors are different types and with their associated filter means are responsive to energy within the wavelength ranges of about 0.8 to about 0.9 microns and about 1.2 to about 1.6 microns respectively.

3. Apparatus according to claim 2, wherein said first detector comprises a silicon detector and is associated with a filter to limit its short wavelength response and the second dectector comprises a germanium detector and is associated with a silicon filter.

4. Apparatus according to claim 3, and including a variable gain amplifier for amplifying the output from the silicon detector before being fed to the comparator means.

* * * * *